(12) United States Patent
Rivera et al.

(10) Patent No.: US 7,030,400 B2
(45) Date of Patent: Apr. 18, 2006

(54) REAL-TIME WEB INSPECTION METHOD AND APPARATUS USING COMBINED REFLECTED AND TRANSMITTED LIGHT IMAGES

(75) Inventors: Nelson M. Rivera, Rochester, NY (US); Mario Errico, Fairport, NY (US); Carl A. Wisniewski, Rochester, NY (US); John P. Kerwawycz, Henrietta, NY (US); William A. Hammond, Rochester, NY (US)

(73) Assignee: Xerox Corporation, Stamford, CT (US)

( * ) Notice: Subject to any disclaimer, the term of this patent is extended or adjusted under 35 U.S.C. 154(b) by 171 days.

(21) Appl. No.: 10/749,768

(22) Filed: Dec. 30, 2003

(65) Prior Publication Data

US 2005/0139792 A1 Jun. 30, 2005

(51) Int. Cl.
*G01N 21/86* (2006.01)
*G01V 8/00* (2006.01)

(52) U.S. Cl. ............................ 250/559.11; 250/559.45; 250/559.01

(58) Field of Classification Search ........... 250/559.45, 250/559.46, 559.11, 559.1
See application file for complete search history.

(56) References Cited

U.S. PATENT DOCUMENTS

| | | | |
|---|---|---|---|
| 5,465,155 A * | 11/1995 | Edgar | 358/500 |
| 5,533,145 A * | 7/1996 | Shofner et al. | 382/141 |
| 6,084,664 A * | 7/2000 | Matsumoto et al. | 356/237.4 |
| 6,157,438 A * | 12/2000 | Kaus | 355/41 |
| 6,236,429 B1 * | 5/2001 | Ho | 348/88 |
| 6,437,312 B1 * | 8/2002 | Adler et al. | 250/216 |
| 6,531,707 B1 | 3/2003 | Favreau et al. | 250/559.46 |
| 6,747,697 B1 * | 6/2004 | Lin et al. | 348/246 |
| 2002/0018201 A1 * | 2/2002 | Young et al. | 356/239.2 |

* cited by examiner

Primary Examiner—Georgia Epps
Assistant Examiner—Brian Livedalen
(74) Attorney, Agent, or Firm—Fay, Sharpe, Fagan, Minnich & McKee, LLP

(57) ABSTRACT

An apparatus and method for web inspection utilize simultaneous capturing of reflected and transmitted light images for real-time merging of same. The reflected light and transmitted light image capturing systems are registered with each other in terms of the down-web and cross-web field being imaged. To allow for the simultaneous acquisition of reflected and transmitted light images, the imaged portion of the web is an unsupported span, and the web is tensioned to prevent sagging. The reflected light and transmitted light image capturing systems each include multiple cameras registered with each other in terms of down-web and cross-web imaging field, and the cameras for the transmitted light image capturing are aligned directly with the light source, which outputs light that is incident on the web at an angle.

5 Claims, 3 Drawing Sheets

REAL-TIME WEB INSPECTION METHOD AND APPARATUS USING COMBINED REFLECTED AND TRANSMITTED LIGHT IMAGES

BACKGROUND

This development relates generally to a web inspection method and apparatus using an improved lighting and camera arrangement. It is described herein with reference to a web inspection method and apparatus for a flexible imaging web such as, e.g., a photoreceptor web used to manufacture photoreceptor belts for electrophotographic imaging systems, but it is not intended to be limited to inspection on any particular type of web material.

In the art of electrophotography, an electrophotographic member comprising a photoconductive insulating layer on a conductive layer is imaged by first uniformly electrostatically charging the imaging surface of the photoconductive insulating layer. The member is then exposed to a pattern of activating electromagnetic radiation such as light, which selectively dissipates the charge in the illuminated areas of the photoconductive insulating layer while leaving behind an electrostatic latent image in the non-illuminated area. This electrostatic latent image may then be developed to form a visible image by depositing finely divided electroscopic toner particles on the surface of the photoconductive insulating layer. The resulting visible toner image can be transferred to a suitable receiving member such as paper. This imaging process may be repeated many times with reusable photoconductive insulating layers.

The electrophotographic member is often in the form of a flexible multilayered photoreceptor belt comprising a substrate, a conductive layer, an optional hole blocking layer, an optional adhesive layer, a charge generating layer, and a charge transport layer and, in some embodiments, an anti-curl backing layer.

As more advanced, higher speed electrophotographic copiers, duplicators and printers have been developed, the electrical and mechanical performance requirements for photoreceptor belts have become more demanding. New digital color and other image-producing products cannot tolerate defects that have been acceptable for previous generation imaging apparatus, such as analog or "light-lens" copiers.

These heightened electrical and mechanical performance requirements are not met when certain defects are located on the surface of or within one or more of the layers of the multilayered belt photoreceptors. These defects are caused by the presence of dirt particles on the substrate, conductive layer, optional hole blocking layer, optional adhesive layer, charge generating layer, charge transport layer and/or optional anti-curl backing layer. Thus for example, particles of dirt (particulate debris) residing on an uncoated or coated substrate surface during application of coatings to form an electrostatographic imaging member, such as a photoreceptor, can cause bubbles or voids to form in the various applied coating layers. It is believed that the dirt particles behave in a manner similar to a boiling chip that initiates solvent boiling at the location of the particle. This local boiling problem is aggravated when a coating solution is maintained near the boiling point of the coating solvent during deposition of the coating or during drying. The formation of bubbles in a coating is particularly acute in photoreceptor charge generation layer coatings and in charge transport layer coatings. Also, dirt particles tend to trap air during application of a coating and the trapped air expands during drying to form an undesirable bubble in the coating. Further, any dirt particles residing on one or both surfaces of an electrophotographic imaging member web substrate or coating thereon can adversely affect adjacent surfaces when the web is rolled up into a roll because the dirt particles cause impressions on the adjacent web surfaces. Because these undesirable impressions can be repeated through more than one overlapping web layer, large sections of a coated web must be scrapped, and this result is highly undesirable.

It should be apparent from the foregoing that it is highly desirable to identify defects in a photoreceptor web before the web is cut and formed into an endless imaging belt. If the defects are identified in advance, it is often possible to cull the defective region from the web so that same does not form part of a finished photoreceptor belt, or to ensure that the defective part of the web is used to manufacture a photoreceptor belt usable for an application where the defect(s) will have no undesired consequences.

It is known to use human inspectors alone or in combination with automated web inspection system in an effort to identify web defects. In one known system, a human operator visually inspects the translucent web as it passes over a light-box. In another embodiment, machine-vision systems are used to acquire images of web moving therepast, and these images are processed according to defect-identification algorithms in an effort to provide an automated web inspection method and apparatus. In known systems of this type, reflected light images and transmitted light images are acquired sequentially and not simultaneously. As such, with conventional web inspection schemes, it is not possible to perform real-time acquisition and analysis of combined transmitted/reflected light images. With conventional system, the sequentially acquired images must be combined off-line, and then processed for image identification and classification. Obviously, this is highly undesired, especially in a process where defects in the web are marked immediately downstream from the inspection process and/or in a process where the web is cut for into sections to be formed into end-products, e.g., photoreceptor belts, immediately downstream from the inspection process.

In light of the foregoing issues, it has been deemed desirable to provide a real-time web inspection method and apparatus using combined reflected and transmitted light images as disclosed herein.

SUMMARY

In accordance with a first aspect of the present development, a web inspection method comprises projecting light from a source to be incident on a select portion of a web that is moving in a down-web direction and that extends laterally to define a width in a cross-web direction. Reflected light from the source that is reflected by the select web portion is captured and a digital image of the reflected light is derived. Simultaneously with the step of capturing reflected light, transmitted light from the source that is transmitted through the select web portion is also captured, and a digital image of the transmitted light is derived. The reflected light digital image and the transmitted light digital image are merged to derive merged image data that represent both the reflected light and the transmitted light. The merged image data are used to identify defects in the web.

In accordance with another aspect of the present development, a web inspection apparatus comprises first and second web supports for movably supporting an associated web moving in a down-web direction. A light source outputs a light pattern adapted to be incident on a select free-span, unsupported portion of the associated web that is located between the first and second web supports. A reflected light image capturing system is provided for imaging the select portion of the associated web based upon light from said source reflected by the select web portion. A transmitted light image capturing system is also provided for imaging the select portion of the associated web based upon light from the source transmitted through the select web portion, wherein the reflected light image capturing system is registered with the transmitted light image capturing system so that the reflected light image capturing system and the transmitted light image capturing system are adapted to simultaneously image the select portion of the associated web in terms of reflected and transmitted light, respectively.

BRIEF DESCRIPTION OF THE DRAWINGS

The development comprises various components and arrangements of components, and comprises various steps and arrangements of steps, preferred embodiments of which are illustrated in the accompanying drawings that form a part hereof and wherein.

DETAILED DESCRIPTION

Figure 1:
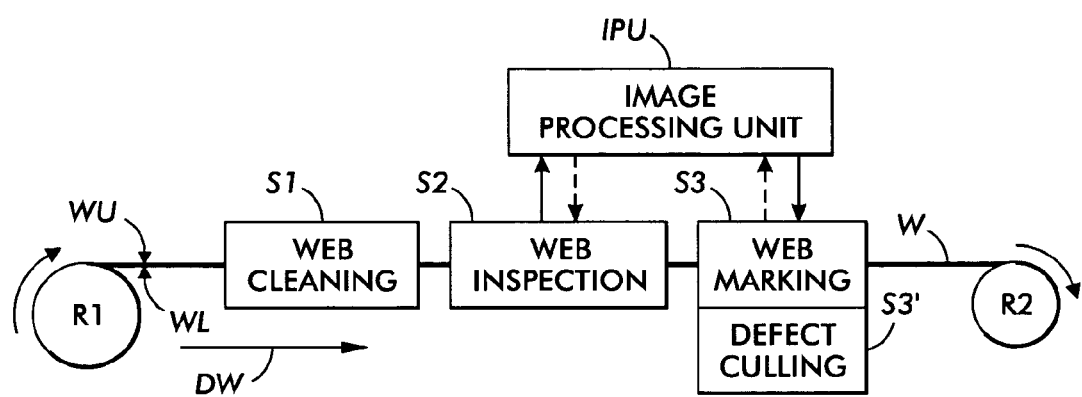
FIG. 1 is a diagrammatic illustration of a real-time web inspection method and apparatus using combined reflected and transmitted light images.

FIG. 1 illustrates a real-time web inspection method and apparatus using combined reflected and transmitted light images in accordance with the present development. In the illustrates embodiment, a web W, e.g., a photoreceptor web, is dispensed from an upstream supply roll or other source R1 and is collected at a storage roll or other storage location R2. The web W thus moves from the supply roll R1 downstream in a down-web direction to the storage roll R2 as indicated by the arrow DW. For ease of reference herein, the term "cross-web" is intended to denote a direction perpendicular or otherwise transverse to the down-web direction DW and parallel to the plane of the web W.

In the illustrated embodiment, the web W moves from the storage roll R1 through a web cleaning station S1 for remove contaminants on its upper surface WU and/or lower surface WL via conventional means such as cleaning rolls and/or other contact or non-contact means. The web W then passes through a web inspection station S2 where it is inspected for defects, and then to web marking station S3 where any defects in the web are marked with labels, ink or any other suitable marking means. In one embodiment, the web marking station S3 is replaced or supplemented by a defect culling station S3' where the defects are cut from the web W before the web is cut into sections that are formed into end-products. The web inspection station S2 and web marking station S3 are operably interconnected to an image processing unit IPU that receives data from the web inspection station S2 and sends data to the web marking station S3 to indicate the portions of the web W to be marked or culled. As indicated with broken lines, data can optionally also flow from the image processing unit IPU to the web inspection station S2 to control same and/or from the web marking station S3 to the image processing station S3 for feedback purposes or the like. In general, the web inspection station S2 and image processing unit IPU cooperate to perform real-time web inspection using combined reflected and transmitted light images in accordance with the present development. The web cleaning station S1, marking station S3 and/or defect culling station S3' are optional but at least one of these is typically provided and used as part of the real-time web inspection method/apparatus.

Figure 2:
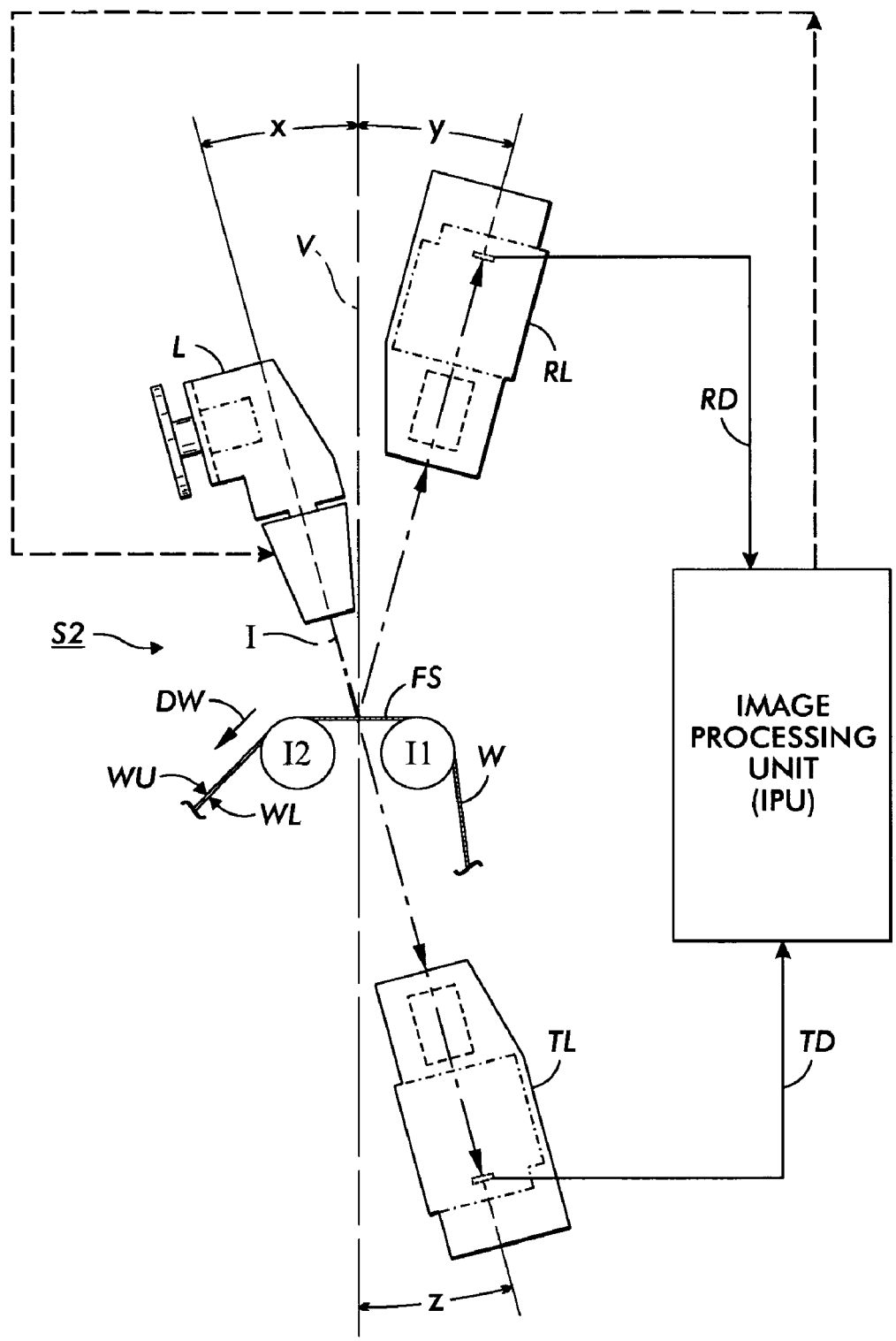
FIG. 2 provides a detailed illustration of the web inspection station of FIG. 1; and, FIG. 3 provides further detailed illustration of the web inspection station and a method for real-time web defect detection.

The web inspection station S2 is disclosed in further detail with reference to FIG. 2. There, it can be seen that the web inspection station S2 comprises first and second web support members such as idler rolls I1, I2 that movably support the web W so that an unsupported free-span web portion FS extends therebetween. The supply and storage rolls R1, R2 (FIG. 1) and/or the web support members I1, I2, control the speed at which the web W moves in the down-web direction DW and control the tension under which the web W is maintained. As such, the free-span FS portion of the web W moves at a known speed and is maintained under known tension. In one example, the web W moves in the down-web direction DW at a speed of 40 feet per minute (fpm) and is maintained under constant tension at one pound per linear inch of width, e.g., if the web extends eighteen inches in the cross-web direction CW (FIG. 3), it is maintained under eighteen pounds of tension at all times. As such, the free-span web portion FS is maintained under sufficient tension to prevent sagging or any other undesired movement thereof.

The web inspection station S2 comprises at least one light source L, at least one reflected light image capturing system RL and at least one transmitted light image capturing system TL. The reflected light and transmitted light image capturing systems RL, TL are operably coupled to the image processing unit IPU as shown, and the light source L is optionally coupled to the image processing unit IPU to be controlled thereby, but need not be. In general terms, the light source L outputs continuous uniform light I that is incident on the free-span web portion FS. The reflected light image capturing system RL receives light R from the source L that is reflected from the free-span web portion FS and derives digital image data that represent the reflected light R (referred to herein as reflected light image data RD), while the transmitted light image capturing system TL simultaneously receives light T from the source L that is transmitted through the free-span web portion FS and derives digital image data that represent the transmitted light T (referred to herein as "transmitted light image data TD"). It can be seen in FIG. 2 that the image data RD, TD are input to the image processing unit IPU for real-time web defect detection and classification in accordance with the present development.

FIG. 2 illustrates a desirable configuration for the light source L and image capturing systems RL, TL in order to implement the method and apparatus of the real-time web inspection development. More particularly, the light I from source L is incident on the free-span web portion FS at an angle x relative to a vertical plane V. The reflected light image capturing system RL is located to receive the reflected light R and is thus arranged on the same side of the web W and positioned at an angle y relative to the vertical plane V, where one of the angles x, y is a positive angle and the other is a negative angle. In one preferred embodiment the angles x and y are equal but opposite angles, i.e., x=−y to provide a "bright-field" system. Alternatively, the angle y can be made larger (more negative) to provide a "twilight" system, where the reflected light image capturing system RL is not directly located in the reflected light field R, but is instead somewhat offset therefrom while still being located therein. The transmitted light image capturing system TL is located on an opposite side of the web W as compared to the reflected light image capturing system RL and is preferably arranged at an angle z relative to the vertical plane V so as to be directly aligned with the light source L and, more particularly, the light I output thereby, i.e., the lens or other light input to the transmitted light image capturing system TL is directly aligned with the axis on which the light I is output from source L. Thus, as shown, x=z so that the transmitted light image capturing system TL lies 180 degrees from the light source L and incident light I so as to receive the transmitted portion T of the light I that passes directly through the free-span web portion FS. As shown in FIG. 2, the light source L and image capturing systems RL, TL are arranged so that x=15 degrees; y=−15 degrees; and, z=15 degrees, but it is not intended that the development be limited to these angles. Also, the illustrated example shows the light I from source L incident on the web upper surface WU, with the reflected light image capturing system RL arranged to capture light R reflected from the web upper surface WU. The light source L can alternatively be arranged to project light I at the lower web surface WL and the reflected light image capturing system RL would then be positioned to capture light R reflected from the lower web surface, with the transmitted light image capturing system TL being located on the opposite side of the web W to capture the transmitted light T.

The reflected light image capturing system RL and transmitted light image capturing system TL must be registered with each other to ensure that the images derived respectively thereby correspond to each other, i.e., to ensure that the systems RL, TL are simultaneously deriving real-time images of the exact same region of the free-span web portion FS in both down-web and cross-web terms. This registration can be accomplished in a variety of different ways. In one example, the web W is provided with known test patterns thereon, and the position of one or both image capturing systems RL, TL is adjusted until the images output by the systems RL, TL are known to be in alignment with each other. Regardless of the registration method used, it is most preferred that the image capturing systems be exactly registered with each other on a pixel-by-pixel basis in both the down web direction DW and cross-web direction CW. One-pixel deviations in both the down-web direction DW and cross-web direction CW are within acceptable tolerance limits. In one embodiment, the reflected light image capturing system RL and transmitted light image capturing system TL are registered with each other with a tolerance of ±1 pixel in both the down-web and cross-web directions DW, CW, wherein the pixels are sized at 25 microns down-web and 25 microns cross-web.

Figure 3:
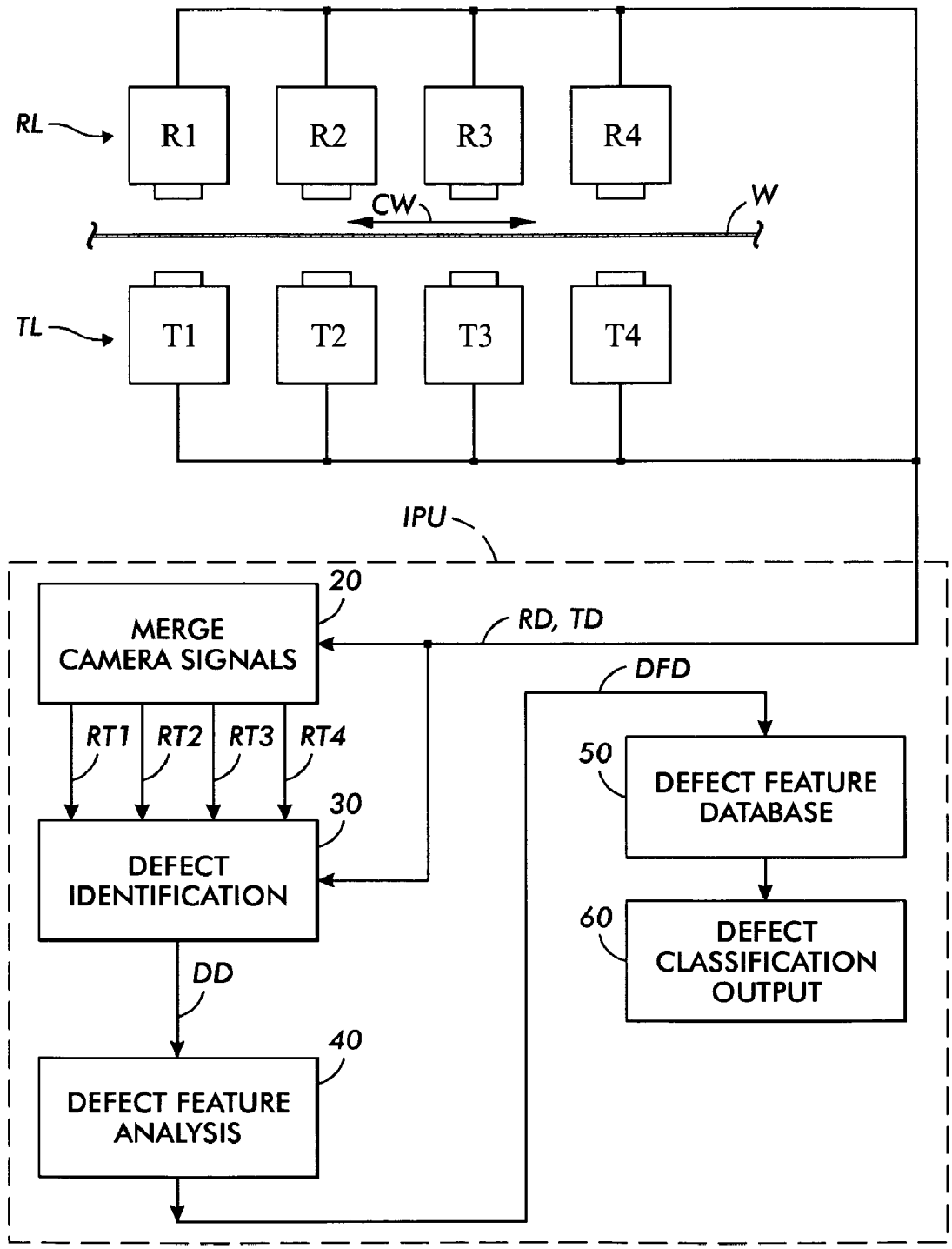

FIG. 3 diagrammatically illustrates the web inspection station S2 and a web inspection method in accordance with the present development. In the illustrated embodiment, the reflected light image capturing system RL comprises at least one and, preferably, a plurality of reflected light image capturing cameras R1–R4 spaced laterally across the web W in the cross-web direction CW. Likewise, the transmitted light image capturing system TL comprises at least one and, preferably, a plurality of transmitted light image capturing cameras T1–T4 spaced laterally across the web W in the cross-web direction CW. The cameras R1–R4 correspond respectively to the cameras T1–T4 so that corresponding pairs of cameras R1, T1; R2, T2; R3, T3; R4, T4 are defined, and the constituents of each pair are registered with each other as described above in terms of both down-web and cross-web imaging locations so that they image the exact same location of the web W, within the ±1 pixel down-web and ±1 pixel cross-web tolerance noted above. The imaging fields for the cameras R1–R4 typically overlap each other in the cross-web direction CW and the imaging fields for the cameras T1–T4 typically overlap each other in the cross-web direction CW to ensure the full cross-web width of the web W is imaged without gaps. Although each group of cameras R1–R4 and T1–T4 is shown as including four cameras, this in not intended to limit the development in any way, and more or less cameras can be used as necessary and/or desired.

The reflected light image cameras R1–R4 are preferably also registered with each other so that the images derived thereby represent an entire cross-web width of the web W having a uniform down-web position. Likewise, the transmitted light image cameras T1–T4 are preferably also registered with each other so that the images derived thereby represent an entire cross-web width of the web W having a uniform down-web position. In the illustrated embodiment, the cameras R1–R4 and T1–T4 are each line-scan CCD cameras so that, when the registration operation is complete, the images derived by the cameras R1–R4 and the cameras T1–T4 represent a 1×m row of pixels, where m is the number of pixels extending in the cross-web direction CW (which varies depending upon the actual width of the web W, the number of cameras and the scanning resolution). It is also preferred that the light source L be defined by a light-line that outputs a light pattern I that extends laterally across the entire width of the web W in the cross-web direction CW, but that extends only minimally in the down-web direction DW. One suitable light source L is a fiber-optic light line, although it is not intended that the development be limited to same.

With continuing reference to FIG. 3, the image processing unit IPU receives the reflected light image data RD and the transmitted light image data TD derived by each camera R1–R4, T1–T4. A step or means 20 merges the cameras signals for each corresponding pair of cameras R1, T1; R2, T2; R3, T3; R4, T4 in real-time and outputs respective merged reflected/transmitted image data signals RT1, RT2, RT3, RT4.

The merged reflected/transmitted image data signals RT1–RT4 are input to a defect identification step or means 30. Preferably, the unmerged original image data RD and TD are also input to the defect identification step or means 30. The defect identification step/means 30 analyzes the input data signals RT1–RT4, (and also the unmerged signals RD, TD if available) and flags any portion thereof as representing a defect if the data vary from known ranges for a non-defective web.

Defect data DD representing web defects as identified by defect identification step/means 30 are input to a defect feature analysis step or means 40 that derives defect feature parameters for each web defect represented in the data DD. In one example, the defect feature analysis step/means 40 derives a list of defect features such as cross-web dimension, down-web dimension, average luminance, maximum and minimum luminance, luminance rate-of-change data, defect shape (e.g., circular, elliptical, etc.), defect location within the web in terms of the cross-web position, and the like. The defect feature analysis step/means 40 is able to derive many defect feature parameters based upon the merged data RT1–RT4 that would not be derivable based upon only the reflected data RD or only the transmitted data TD. With the combined reflected/transmitted light web imaging method described herein, it becomes possible to distinguish defects that appear similar in one lighting configuration, but that appear different in the other lighting configuration.

For each web defect represented by the data DD, the defect feature analysis step/means 40 outputs defect feature data DFD to a defect feature database step or means 50. The defect feature data DFD for each web defect are input to the defect feature database 50, which can be a look-up table, a histogram matching algorithm, or other database matching means/operation, and the defect feature database 50 outputs a defect classification output value 60 that describes the defect as being a particular type of defect, e.g., surface dirt, an internal bubble, a scratch, a dimple, a bump, etc. The defect classification output value 60 is used by the image processing unit IPU to control the web marking/defect culling station S3, S3' depending upon the type or defect. For example, if the web W is intended for a high-performance application, the image processing unit can control the web marking/defect culling station S3, S3' to mark the relevant portion of the web as defect and or to cull the defective portion from the web. On the other hand, if the web is intended for a low-performance application and the defect value 60 indicates a minor defect, the image processing unit IPU can control the web marking/defect culling station S3, S3' to take no action.

The image processing unit IPU is provided by any suitable circuit and/or programmed computing apparatus suitable for digital image processing such as a dedicated circuit or a specially programmed personal computer. Suitable image processing units IPU are available commercially from Cognex Corporation, Natick, Mass. (one such unit was formerly sold under the tradename ISYS 2000), and other imaging processing units from the same or other sources can be used.

As used herein, the term "real-time" is intended to mean processing data without off-line storage thereof and subsequent retrieval of the data for later processing so that the merged reflected/transmitted light data signals RT1–RT4 are immediately available for processing before the relevant portion of the web W passes through the web marking/defect culling station S3, S3'.

Modifications and alterations will occur to those of ordinary skill in the art, and it is intended that the following claims be construed literally and/or according to the doctrine of equivalents to encompass all such modifications and alterations to the fullest extent possible.

The invention claimed is:

1. A web inspection method comprising:

projecting light from a source to be incident on a select portion of a web that is moving in a down-web direction and that extends laterally to define a width in a cross-web direction, wherein said select portion of said web comprises an unsupported free-span portion of said web that extends and is moving between first and second spaced-apart idler rolls, wherein said web moves in said down-web direction while being maintained under a select tension of at least one pound of tension for each inch of said width of said web;

using a reflected light image capturing camera system to capture reflected light from said source that is reflected by said select web portion and deriving a digital image of said reflected light;

simultaneously with said step of capturing reflected light, using a transmitted light image capturing camera system to capture transmitted light from said source that is transmitted through said select web portion and deriving a digital image of said transmitted light;

wherein said light source and said reflected light image capturing system are located on a first side of said web and wherein said transmitted light image capturing system is located on a second side of said web that is opposite said first side so that said web passes between said light source and said transmitted light image capturing system;

wherein said light projected from said source is incident on said web at an angle of x degrees relative to a vertical plane, said reflected light image capturing system is located at an angle y relative to said vertical plane, and wherein said transmitted light image capturing system is directly aligned with said projected light;

wherein said reflected light image capturing system comprises a plurality of reflected light imaging cameras with overlapping reflected light imaging fields in said cross-web direction that are registered with each other in said down-web direction, and wherein said transmitted light image capturing system comprises a plurality of transmitted light imaging cameras with overlapping transmitted light imaging fields in said cross-web direction that are registered with each other in said down-web direction, and wherein each of said reflected light imaging cameras corresponds to and is registered with one of said transmitted light imaging cameras so as to define a corresponding pair of imaging cameras located on opposite sides of said web;

digitally merging said reflected light digital image and said transmitted light digital image to derive merged image data that represent both said reflected light and said transmitted light;

using all of: (i) said reflected light digital image; (ii) said transmitted light digital image; and, (iii) said merged image data to identify defects in said web;

without interrupting movement of said web in said down-web direction, physically marking said web at or near all identified defects to define marked defects;

culling said marked defects from said web.

2. The method as set forth in claim 1, wherein said light source comprises a fiber-optic light line.

3. The method as set forth in claim 2, wherein each of said reflected light cameras and each of said transmitted light cameras comprises a line-scan CCD camera.

4. The method as set forth in claim 3, wherein said reflected light cameras are registered with each other in terms of a down-web portion of said web being imaged respectively thereby so that said reflected light imaging cameras cooperate to image a single uninterrupted 1×m pixel row of said web, where m is the resolution of pixels used to image an entire crossweb dimension of said web.

5. The method as set forth in claim 4, wherein said transmitted light cameras are registered with each other in terms of a down-web portion of said web being imaged respectively thereby so that said transmitted light imaging cameras cooperate to image a single uninterrupted 1×m pixel row of said web, where in is the resolution of pixels used to image an entire cross-web dimension of said web.

* * * * *